US007935685B2

(12) United States Patent
Giordano et al.

(10) Patent No.: US 7,935,685 B2
(45) Date of Patent: May 3, 2011

(54) PROCESS FOR PREPARATION OF INCLUSION COMPOUNDS BETWEEN A NON-STEROIDAL ANTI-INFLAMMATORY DRUG AND BETACYCLODEXTRIN BY MICROWAVE TREATMENT

(75) Inventors: Ferdinando Giordano, Parma (IT); Ruggero Bettini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 546 days.

(21) Appl. No.: 10/499,338

(22) PCT Filed: Dec. 17, 2002

(86) PCT No.: PCT/EP02/14349
§ 371 (c)(1),
(2), (4) Date: Oct. 6, 2006

(87) PCT Pub. No.: WO03/053475
PCT Pub. Date: Jul. 3, 2003

(65) Prior Publication Data
US 2005/0042471 A1 Feb. 24, 2005
US 2007/0059547 A9 Mar. 15, 2007

(30) Foreign Application Priority Data

Dec. 21, 2001 (IT) .............................. MI2001A2749

(51) Int. Cl.
| | |
|---|---|
| *A01N 43/04* | (2006.01) |
| *A61K 31/715* | (2006.01) |
| *A61K 31/70* | (2006.01) |
| *C07D 279/00* | (2006.01) |
| *C07D 285/00* | (2006.01) |
| *C07D 295/00* | (2006.01) |
| *C07D 419/00* | (2006.01) |
| *C07D 513/00* | (2006.01) |

(52) U.S. Cl. ................................ 514/58; 514/25; 544/14
(58) Field of Classification Search .................. 514/58, 514/25; 544/14
See application file for complete search history.

(56) References Cited

U.S. PATENT DOCUMENTS

| | | | | |
|---|---|---|---|---|
| 5,164,380 A | * | 11/1992 | Carli et al. ...................... 514/58 |
| 5,472,954 A | * | 12/1995 | Loftsson ......................... 514/58 |
| 5,594,125 A | * | 1/1997 | Seyschab et al. ............. 536/103 |
| 5,665,767 A | | 9/1997 | Fischer et al. |
| 5,854,226 A | | 12/1998 | Penkler et al. |

FOREIGN PATENT DOCUMENTS

| | | | |
|---|---|---|---|
| EP | 0852140 | | 7/1998 |
| WO | WO 95/32737 | * | 7/1995 |
| WO | 02/13792 | | 2/2002 |

OTHER PUBLICATIONS

H Sucker, P Fuchs, P Speiser: "Pharmazeutische Technologie", Georg Thieme Verlag, Stuttgart New York, XP002232157, p. 442, paragraph 2.3.3-p. 443, (1991).
Y. Rossetto: "Pharmacotechnie industrielle Phi 41", GREPIC IMT, XP002232158, p. 249, paragraph 5.3.3, (1998).
Loftsson: "Pharmaceutical applications of beta-cyclodextrin" Pharmaceutical Technology Europe, vol. 11, No. 10, 1999, pp. 20-32, XP002232156, UK, the whole document.

* cited by examiner

*Primary Examiner* — Shaojia Anna Jiang
*Assistant Examiner* — Scarlett Goon
(74) *Attorney, Agent, or Firm* — Oblon, Spivak, McClelland, Maier & Neustadt, L.L.P.

(57) ABSTRACT

A process for the preparation of inclusion complexes of a drug (piroxicam or ibuprofen) and a cyclodextrin, characterised in that: a) the drug and cyclodextrin, in the form of finely divided powders, are mixed in the presence of aqueous or hydroalcoholic solutions, ammonia solutions or acid solutions; b) the resulting mixture is treated in a microwave oven; c) the resulting product is dried under vacuum at room temperature or with heating.

16 Claims, No Drawings

US 7,935,685 B2

PROCESS FOR PREPARATION OF INCLUSION COMPOUNDS BETWEEN A NON-STEROIDAL ANTI-INFLAMMATORY DRUG AND BETACYCLODEXTRIN BY MICROWAVE TREATMENT

CROSS REFERENCES TO RELATED APPLICATIONS

This application is a 371 of International Patent Application No. PCT/EP02/14349, filed on Dec. 17, 2002, and claims priority to Italian Patent Application No. MI2001A002749, filed on Dec. 21, 2001.

SUMMARY

The present invention relates to a new process for the preparation of inclusion compounds of drugs and cyclodextrins.

According to the invention, powdered components are mixed to form a suitable aqueous or hydroalcoholic suspension. The suspension is subjected to microwave treatment, and the resulting product, which contains the drug mainly or wholly in amorphous form, possesses physical, technological and biopharmaceutical characteristics suitable for the preparation of solid pharmaceutical forms.

In particular, the process of the invention produces inclusion complexes of drugs and cyclodextrin which are more wettable, have a greater equilibrium solubility, and dissolve faster in an aqueous medium than the crystalline drug. This means more favourable pharmacokinetics, and consequently leads to better therapeutic results.

PRIOR ART

Many substances used as active ingredients (drugs) are characterised by a low ability to interact with water, and in particular by low wettability, low solubility and slow dissolution rate. These characteristics have adverse effects on the bioavailability of the drug when it is not administered systemically. Indeed, drugs which are slowly and variably absorbed by the gastrointestinal mucosa present fluctuating blood levels after oral or rectal administration, and the appearance of the blood peak is delayed. As a consequence, the drug may exhibit a reduced therapeutic efficacy and/or it may also show, after absorption a significant intra- and inter-subjects variability. This behaviour may also give rise to adverse side-effects such as gastric damage in the case of acid drugs, caused by prolonged contact between the poorly soluble drug and the mucosa. Sufficient solubility in water is also a pre-requisite for the manufacture of liquid formulations in solution.

In view of the problems described above, it is very useful to employ methods that improve the solubility properties of drugs which are intrinsically poorly soluble in water.

The low ability of a substance to interact with water depends mainly on the chemical nature of the substance, and also on chemico-physical characteristics such as the crystalline or amorphous structure of the substance and its particle size.

Some examples of modifications of the chemical nature of poorly soluble drugs to increase their solubility, for example by formation of salts, have been reported in the pharmaceutical industry (Berge et al. *J Pharm Sci* 1977, 66, 1-19; Ceppi Monti et al. *Arzneimittel Forschung* 1992, 42, 556-559).

The micronisation process is also used to increase the surface area of the drug, and consequently the part of surface in contact with the solvent. However, although this treatment increases the dissolution rate in some cases, it does not usually increase solubility.

An interesting way of increasing the solubility and dissolution rate of poorly soluble active ingredients is represented by the formation of complexes with cyclodextrins, namely cyclic oligosaccharides obtained by hydrolysis and enzymatic cyclisation of starch. The main natural cyclodextrins ($\alpha$, $\beta$, and $\gamma$) are formed by six, seven and eight glucopyranose molecules respectively, linked by $\alpha$-1,4 bonds to form a ring. Several hundreds of semi-synthetic derivatives have also been produced.

The techniques so far devised for preparing these complexes can be applied in solution or in the solid phase.

The method for the preparation of complexes in solution requires the preparation of an aqueous solution of cyclodextrin, to which the drug to be included is added as such, or as a solution. The suspension (or solution) thus obtained is left to equilibrate under continuous stirring, then filtered, and the complex is recovered by removing the solvent by evaporation (for example by spray-drying, Tokomura et al. *Yakuzaigaku* 1985, 45, 1-6) or sublimation (lyophilisation, Kurozumi et al. *Chem Pharm Bull* 1975, 23, 3062-3068). For example, EP 153998, in the applicants' name, describes the preparation of a piroxicam/beta-cyclodextrin complex by lyophilisation of an aqueous solution of the components in a molar ratio of 1:2.5.

Coprecipitation is the method most commonly used for small-scale production of complexes. A hot aqueous solution of cyclodextrin is prepared, and a suitable amount of "guest" (the substance to be included) is added, following which the mixture is cooled to room temperature. The solid complex precipitates during the cooling stage.

The "kneading" method requires energetic mixing of cyclodextrin and the drug with a small amount of a suitable solvent, which is eliminated when the mixture is dried. For example, patent application WO 95/32737, in the name of SAD, discloses a method for the production of complexes of non-steroidal anti-inflammatory drugs and beta-cyclodextrin, based on obtaining a paste and drying it to produce the inclusion complex.

Moreover, as already mentioned, complexes can also be obtained without the aid of solvents, for example by co-grinding. The physical mixture of drug and cyclodextrin is prepared and ground in high-energy mills under controlled humidity conditions (RH=60-75%), with or without heating. An amorphous complex is usually formed.

For example EP 449167, also filed in the applicant's name, discloses a process for the preparation of a piroxicam: $\beta$-cyclodextrin complex wherein the two components, in powder form, are pre-mixed and then co-ground in a high-energy mill in the presence of steam.

Although many of these techniques can also be used on an industrial scale, they often involve time-consuming manufacturing processes and large amounts of solvent; in addition, processes running continuously are not possible. Therefore there is a need for faster and more convenient processes for the preparation of cyclodextrins on an industrial scale.

DESCRIPTION OF THE INVENTION

Analysis of the approaches described in the cited literature demonstrates that modification of the chemico-physical properties of a poorly soluble active ingredient by complexation with cyclodextrin produces good results in terms of the biopharmaceutical behaviour of said ingredient. In particular, an increase in the dissolution rate compared with the pure drug increases the bioavailability of the product, and consequently produces better therapeutic results.

The need for faster, more convenient methods of manufacturing complexes with cyclodextrins on an industrial scale also emerges.

Microwaves are electromagnetic waves similar to radio waves, with a frequency of between 300 MHz and 300 GHz.

The operating frequencies used for industrial, scientific and domestic purposes are 915 and 2450 MHz. The highest value is used, for example, for drying processes performed under vacuum (Waldrom et al. *Pharm Eng* 1988, 8, 9-13).

When a substance is placed in an electrical field in the presence of radio waves or microwaves, it is heated evenly due to polarisation of the individual molecules.

The principle on which dielectric heating is based is energy absorption by permanent and induced dipoles. As a result of this absorption, the molecules start to vibrate, and their friction generates heat (Vromans et al. *Eur J Pharm Biopharm* 1994, 40, 333-336).

Not all molecules have suitable structures for this energy absorption. In general, polar substances with a high dielectric constant absorb more energy than non-polar materials. However, the intensity of the resulting vibration also depends partly on the structure of the molecules (shape and size), the viscosity of the material, the temperature and the intermolecular bonds.

Applications of microwaves in various industrial fields are attracting increasing interest due to the possibility of energy saving, environmental protection and cost savings. More rational energy use means lower costs and greater manufacturing efficiency.

The first industrial process in the field of foodstuffs used this energy source to dry potato crisps in 1960. The use of microwaves during continuous production increased productivity and reduced production times, the space needed for manufacture and energy costs.

By 1986 over 130 food manufacturers were using microwaves in their manufacturing processes (to dry pasta, pasteurise yoghurt, etc.).

Microwaves were introduced somewhat later into the chemical industry in general and the pharmaceutical industry in particular, but applications are rapidly increasing; they include some interesting uses in the fields of extraction, evaporation, protein hydrolysis, determination of percentage moisture contents, pyrolysis, polymerisation, catalysis and combinatorial chemistry, which offer great advantages in terms of speed of performance, possibility of autosampling, interfacing with analysis systems, etc.

The present invention relates to a method of preparing inclusion complexes with favourable biopharmaceutical and technological characteristics by means of microwave treatment of mixtures in aqueous or hydroalcoholic suspension containing a drug and a natural or semi-synthetic cyclodextrin.

The process according to the invention, as defined in the main and dependent claims, produces inclusion complexes, mainly or wholly in dissolved form, with good dissolution kinetics, whose chemical purity remains unchanged. The formation of an inclusion complex is demonstrated by the disappearance of the melting peak of the active ingredient after thermal analysis (Frömming & Szejtli in *Cyclodextrins in Pharmacy*, Kluwer Academic Publishers, 1994). Cyclodextrins with an initial water content above 4% will preferably be used, because initial amounts below 4% by weight make complete complexation of the drug difficult. The time of exposure to radiation and the maximum power are regulated as specified hereinafter, to promote the formation of inclusion complexes and ensure that the chemical (and physical) stability of the components is not jeopardised. As cyclodextrins are sugars, they are liable to thermal degradation processes (caramelisation), and in some cases accelerate the degradation rate of the active ingredients included (Backensfeld et al. *Int J Pharm* 1991, 74, 85-93; Glass et al. in Proceedings of the 8$^{th}$ International Symposium on Cyclodextrins, 1996, Kluwer Academic Publishers, pp. 287-290).

WO 97/06781, in the name of Nissan Chemical, relates to high-frequency mechanical/chemical heating processes (e.g. microwave ovens) used to prepare solid dispersions of drugs which are poorly soluble in water or characterised by slow dissolution kinetics, in the presence of agents able to stabilise the amorphous state such as polymers and cyclodextrins. The products thus obtained are characterised by a high rate of absorption through the mucous membranes, which makes it possible to increase the bioavailability of the drug. Some examples of solid dispersions obtained by microwave treatment at 500 or 700 W have been reported, but none of them use cyclodextrins.

Kerc J et al. (*Drug Dev Ind Pharm* 1998, 24, 359-363) described the preparation of solid dispersions of felodipine, a poorly soluble drug, in a water-soluble carrier such as porous (amorphous) $SiO_2$ or NaCl (crystalline), by mixing and heating in a dryer under vacuum (at 100° C. and $0.01 \cdot 10^5$ Pa) or in a microwave oven at maximum power (500 W) at different times.

Bettinetti et al., World Meet. Pharm, Biopharm Pharm Technol 591-2, 1995, described the application of microwaves (with energy ≦500W) to α-cyclodextrin, but only to eliminate residual and/or crystallisation water.

As it can be observed, none of those documents describe inclusion complexes, still less do they refer to the special operating conditions needed to aid complexation and prevent the degradation processes referred to above.

A further aspect of this invention relates to pharmaceutical compositions comprising inclusion complexes of drugs and cyclodextrin obtained by the process claimed, in combination with additives and/or excipients commonly used in the pharmaceutical industry.

DETAILED DESCRIPTION OF THE INVENTION

The characteristics of the process of the invention, the products obtained and the corresponding pharmaceutical compositions will be described in the following detailed description.

Said process is based on rapid drying caused by the heating effect of microwave radiation, under controllable vacuum conditions.

During the first stage, the drug and cyclodextrin, in the form of finely divided powders, are mixed with a turbine mixer such as the Ultraturrax together with a small amount of water or aqueous solutions of alcohols (preferably ethanol), acids (preferably HCl) or bases (preferably ammonia).

By "small amounts" of water or solutions we mean percentages by weight on the drug and cyclodextrin mixture amounting to between 20 and 80%, and preferably between 40 and 60%.

During the second stage, the resulting mixture is treated in a microwave oven. During the third stage, the product obtained is dried under vacuum at room temperature or with gentle heating.

The maximum exposure time to radiation and the maximum power which can be administered must be determined experimentally for each drug/cyclodextrin mixture. The treatment is usually performed by applying a radiation power of between 100 and 800 W, preferably between 400 and 600 W, and even more preferably 450 W. The treatment is carried out for between 1 and 60 minutes, and preferably between 2 and 10 minutes. Drying is carried out for between 2 and 60 minutes, preferably between 5 and 30 minutes, at a temperature below 50° C.

The preferred active ingredients are drugs that are poorly soluble in water or characterised by slow dissolution kinetics. Examples of poorly soluble drugs which can be made more bioavailable upon inclusion complex formation are non-steroidal anti-inflammatory drugs such as piroxicam, ibuprofen, ketoprofen, calcium antagonists such as nifedipine and nicardipine, anticonvulsants such as carbamazepine and phenytoin, and oral hypoglycemics such as tolbutamide and glibenclamide.

Any natural cyclodextrin, such as α-, β- or γ-cyclodextrin, can be used, preferably β-cyclodextrin or a semi-synthetic cyclodextrin such as hydroxypropyl-β-cyclodextrin. Cyclodextrin should preferably have an initial water content above 4% by weight.

The molar ratio of the drug to cyclodextrin can range between 10:1 and 1:100, preferably between 5:1 and 1:50, and more preferably between 1:1 and 1:5.

The inclusion complex obtained by the process of the invention can be formulated as solid or liquid preparations and preferably as tablets, employing additives and excipients commonly used in the pharmaceutical industry.

The invention is further illustrated by the following examples.

Example 1

Piroxicam:β-cyclodextrin Inclusion Complex

Preparation of Physical Mixture

Approx. 10 g of piroxicam (PRX) and 92 g of β-cyclodextrin (βCD), corresponding to a molar ratio of 1:2.5, were accurately weighed.

The two powders were combined and thoroughly mixed to ensure uniform distribution of the particles.

After the addition of water (approx. 70 mL) and 28% ammonia (1.5 mL), the physical mixture was mixed with an Ultraturrax turbine mixer for 5 minutes at 9500 rpm.

Microwave Treatment

Three samples of approx. 25 grams each were taken from the creamy paste thus obtained. The samples were placed in crystallisers, covered with fibreglass discs to prevent sprinkling in the oven, and treated with microwaves in accordance with the following operational pattern:

TABLE 1

Parameters relating to microwave treatment of three samples of PRX-βCD-$H_2O$-$NH_3$ mixture.

| PRX:βCD | Time | Power (W) | Vacuum (mbar) |
|---|---|---|---|
| Stage 1 | 5 min 30 s | 450 | ~250 |
| Stage 2 | 5 min | 0 | ~190 |

Stage 2, also known as the "dry stage", corresponds to vacuum values of ~190 mbar without microwave radiation. These conditions, together with the residual heat, enable the residual water in the sample to be eliminated very quickly.

The samples weighed after the microwave treatment showed an average weight loss of approx. 40%.

The thermal analysis tracings of the samples, prepared by microwave treatment, show that the piroxicam melting peak disappears at approx. 200° C.

The solids recovered from the crystallisers were subjected to further grinding in a mortar to test the stability of the complex to mechanical stresses. The tracings show no differences from those obtained before grinding.

Determination of the Dissolution Rate of Piroxicam from the Solid Phases Obtained.

The dissolution rate of the samples under study was determined by the dispersed amount method according to the USP 25, NF 20, 2002. The test samples were introduced into vessels containing 1 L of distilled water each.

The test was conducted by maintaining the temperature of the dissolving bath at 37° C. and regulating the paddle rotation speed to 50 rpm.

The concentration of the drug in solution was determined at 2-minute intervals by spectrophotometry.

Samples containing equivalent amounts of PRX (approx. 20 mg) were analysed:
1. sample of PRX (approx. 20 mg), code PRX;
2. sample of the 1:2.5, mol:mol physical mixture of PRX-βCD (approx. 200 mg), code M.F.;
3. sample of the mixture obtained after microwave treatment (approx. 200 mg), code PROD.

Each sample was analysed in triplicate.

The amount dissolved and the corresponding percentage compared with the initial dose of PRX in the sample are set out in Table 2.

As it can be appreciated, piroxicam dissolves faster and in larger amounts from the inclusion complex obtained by microwave treatment.

TABLE 2

| T (min) | mg diss. PROD | mg diss. M.F. | mg diss. PRX | % DISS PROD | % DISS M.F. | % DISS PRX |
|---|---|---|---|---|---|---|
| 0 | 0 | 0 | 0 | 0 | 0 | 0 |
| 2 | 6.376 | 0.793 | 0.011 | 26.778 | 3.324 | 0.052 |
| 4 | 8.437 | 1.881 | 0.054 | 35.436 | 7.885 | 0.245 |
| 6 | 10.218 | 3.063 | 0.100 | 42.915 | 12.841 | 0.451 |
| 8 | 11.764 | 4.563 | 0.137 | 49.408 | 19.129 | 0.619 |
| 10 | 13.135 | 6.161 | 0.189 | 55.168 | 25.826 | 0.851 |
| 20 | 17.481 | 10.916 | 0.455 | 73.421 | 45.759 | 2.051 |
| 30 | 19.998 | 13.198 | 0.741 | 83.991 | 55.324 | 3.340 |
| 40 | 21.315 | 15.119 | 1.042 | 89.522 | 63.377 | 4.694 |
| 50 | 21.701 | 16.734 | 1.351 | 91.145 | 70.145 | 6.087 |
| 60 | 21.810 | 17.991 | 1.695 | 91.602 | 75.414 | 7.635 |

Example 2

Ketoprofen:β-cyclodextrin Inclusion Complex

Preparation of Physical Mixture

Approx. 2 g of ketoprofen (keto) and 9.960 g of β-cyclodextrin, corresponding to a molar ratio of 1:1, were accurately weighed.

The two powders were thoroughly mixed to ensure homogeneous dispersion.

After the addition of water (~8 mL), the physical mixture obtained was mixed with an Ultraturrax for 3 minutes at 8000 rpm.

Microwave Treatment

Three samples of approx. 5 g each were prepared, placed in crystallisers and subjected to microwave treatment. As the amount of substance to be dried is directly proportional to the exposure time to microwaves, when the amount of substance for each sample was reduced, the heating times were also reduced.

The procedure followed is summarised in Table 3.

TABLE 3

Parameters relating to microwave treatment of three samples of Keto-βCD-H₂O mixture.

| Keto:βCD | Time | Power (W) | Vacuum (mbar) |
|---|---|---|---|
| Stage 1 | 2 min 30 s | 450 | ~250 |
| Stage 2 (Dry) | 3 min | 0 | ~190 |

The samples, weighed after the microwave treatment, showed an average weight loss of approx. 44%.

The calorimetric analysis performed on the dried samples showed that the melting peak of ketoprofen at approx. 96° C. disappears.

Example 3

Ketoprofen:hydroxypropyl-β-cyclodextrin Inclusion Complex

Preparation of Physical Mixture

Approx. 2 g of ketoprofen and 10.5 g of cyclodextrin, corresponding to a molar ratio of 1:1, were accurately weighed.

The two powders were mixed until a homogenous dispersion was obtained; water (~5.5 mL) was added to the dispersion, and the resulting mixture was treated with an Ultraturrax for 3 minutes a 8000 rpm.

Microwave Treatment

Three samples taken from the resulting mixture, amounting to approx. 4 g each, were subjected to microwave treatment in accordance with the method described herein.

TABLE 4

Parameters relating to microwave treatment of three samples of ketoprofen/hydroxypropyl-β-cyclodextrin mixture.

| Keto/HPβCD | Time | Power (W) | Vacuum (mbar) |
|---|---|---|---|
| Stage 1 | 2 min 30 s | 450 | ~250 |
| Stage 2 (Dry) | 3 min | 0 | ~190 |

The samples lost an average of 30% by weight after this operation; once again, the melting peak of the active ingredient disappeared.

Example 4

Ibuprofen:β-cyclodextrin Inclusion Complex

Preparation of Physical Mixture

Approx. 2 g of ibuprofen (Ibu) and 19.1 g of β-cyclodextrin, corresponding to a molar ratio of 2:3, were accurately weighed.

The powders were mixed; approx. 13 mL of water was then added to the physical mixture, followed by stirring with an Ultraturrax for 4 minutes a 9500 rpm.

Microwave Treatment

Three samples of approx. 6 g each were prepared, placed in crystallisers, covered with discs and subjected to microwave treatment.

TABLE 5

Parameters relating to microwave treatment of three samples of Ibu-βCD-H₂O mixture.

| Ibu:β-CD | Time | Power (W) | Vacuum (mbar) |
|---|---|---|---|
| Stage 1 | 2 min 30 s | 450 | ~250 |
| Stage 2 (Dry) | 3 min | 0 | ~190 |

By the end of the process the samples had lost an average of 35% by weight.

The results of thermal analysis show that the melting peak of the active ingredient at approx 76° C. disappears.

Example 5

Carbamazepine:β-cyclodextrin Inclusion Complex

Preparation of Physical Mixture

Approx. 2 g of carbamazepine (CBZ) and 11.3 g of β-cyclodextrin, corresponding to a molar ratio of 1:1, were accurately weighed.

~10 mL of water was then added to the physical mixture obtained, followed by treatment with an Ultraturrax for approx. 2 minutes a 9500 rpm.

Microwave Treatment

Three samples of the resulting mixture, amounting to approx. 5 g each, were placed in crystallisers and subjected to microwave treatment as described in Table 6.

TABLE 6

Parameters relating to microwave treatment of three samples of CBZ-βCD-H₂O mixture.

| CBZ:β-CD | Time | Power (W) | Vacuum (mbar) |
|---|---|---|---|
| Stage 1 | 2 min 30 s | 450 | approx. 250 |
| Stage 2 (Dry) | 3 min | 0 | approx. 190 |

By the end of the process the samples had lost an average of 47% by weight.

The results of thermal analysis show a drastic reduction in the two melting peaks of the two polymorphic forms of carbamazepine, although traces of the crystalline active ingredient are still present.

The invention claimed is:
1. A process for making an inclusion complex of a poorly water soluble non-steroidal anti-inflammatory drug and a cyclodextrin, said process comprising:
   (a) mixing said drug and said cyclodextrin, in the form of finely divided powders, in the presence of a small amount of water or an aqueous solution of one or more components selected from the group consisting of an alcohol, an acid, and a base, to obtain a mixture consisting essentially of said drug, said cyclodextrin, and said water or said aqueous solution;
   (b) treating said mixture in a microwave oven, at radiation power of from 100 to 800 W for a time of 1 and 60 minutes, to obtain a treated product; and
   (c) drying said treated product under vacuum at room temperature or with heating at a temperature below 50° C.;
   wherein:
   the mixture contains water or the aqueous solution in an amount of 20 to 80% by weight; and
   the dried product is in amorphous form.

2. A process as claimed in claim 1, wherein said treating said mixture in a microwave oven is carried out at a radiation power of between 400 and 600 W for a time of between 1 and 60 minutes.

3. A process as claimed in claim 1, wherein said treating said mixture in a microwave oven is carried out at a radiation power of 450 W for a time of between 2 and 10 minutes.

4. A process as claimed in claim 3, wherein said drug is selected from the group consisting of piroxicam and ibuprofen.

5. A process as claimed in claim 1, wherein said drug and said cyclodextrin are mixed in a molar ratio of said drug to said cyclodextrin between 10:1 and 1:100.

6. A process as claimed in claim 1, wherein said drug and said cyclodextrin are mixed in a molar ratio of said drug to said cyclodextrin between 1:1 and 1:5.

7. A process as claimed in claim 1, wherein said mixture contains water in an amount of 40 to 60% by weight.

8. A process as claimed in claim 1, wherein said mixture contains water in an amount of 20 to 80% by weight.

9. A process as claimed in claim 1, wherein said mixture contains water in an amount of 40 to 60% by weight.

10. A process for making an inclusion complex of a poorly water soluble non-steroidal anti-inflammatory drug and a cyclodextrin, said process comprising:
 (a) mixing said drug and said cyclodextrin, in the form of finely divided powders, in the presence of a small amount of water or an aqueous solution of one or more components selected from the group consisting of an alcohol, an acid, and a base, to obtain a mixture consisting of said drug, said cyclodextrin, and said water or said aqueous solution;
 (b) treating said mixture in a microwave oven, at radiation power of from 100 to 800 W for a time of 1 and 60 minutes, to obtain a treated product; and
 (c) drying said treated product under vacuum at room temperature or with heating at a temperature below 50° C.;
 wherein:
 the mixture contains water or the aqueous solution in an amount of 20 to 80% by weight; and
 the dried product is in amorphous form.

11. A process as claimed in claim 10, wherein said treating said mixture in a microwave oven is carried out at a radiation power of between 400 and 600 W for a time of between 1 and 60 minutes.

12. A process as claimed in claim 10, wherein said treating said mixture in a microwave oven is carried out at a radiation power of 450 W for a time of between 2 and 10 minutes.

13. A process as claimed in claim 10, wherein said drug is selected from the group consisting of piroxicam and ibuprofen.

14. A process as claimed in claim 10, wherein said drug and said cyclodextrin are mixed in a molar ratio of said drug to said cyclodextrin between 10:1 and 1:100.

15. A process as claimed in claim 10, wherein said drug and said cyclodextrin are mixed in a molar ratio of said drug to said cyclodextrin between 1:1 and 1:5.

16. A process as claimed in claim 10, wherein said cyclodextrin has a water content above 4% by weight prior to said mixing.

* * * * *